United States Patent [19]

Chawla et al.

[11] Patent Number: 5,239,991
[45] Date of Patent: Aug. 31, 1993

[54] DISPOSABLE POWDER MEDICAMENT INHALATION DEVICE WITH PEEL-OFF COVER

[75] Inventors: Brindra P. S. Chawla, Nottingham; Andrew R. Clark, Leicestershire, both of England

[73] Assignee: Fisons plc, England

[21] Appl. No.: 887,108

[22] Filed: May 19, 1992

Related U.S. Application Data

[63] Continuation of Ser. No. 541,916, Jun. 21, 1990, abandoned.

[30] Foreign Application Priority Data

Jun. 21, 1989 [GB] United Kingdom ............... 8914223

[51] Int. Cl.$^5$ ............... A61M 15/00; A61M 16/00; B05D 7/14; B65D 83/06
[52] U.S. Cl. ............... 128/203.15; 128/203.12; 206/539
[58] Field of Search ............... 128/203.12, 203.13, 128/203.15, 204.11, 203.23, 203.14; 206/363, 530, 532, 534.1, 534.2, 538, 539; 220/23.4

[56] References Cited

U.S. PATENT DOCUMENTS

| | | | |
|---|---|---|---|
| 263,451 | 8/1882 | Adams | 128/203.15 |
| 361,748 | 4/1887 | Culbertson | 128/203.15 |
| 390,455 | 10/1888 | Cleaveland | 128/203.15 |
| 545,679 | 9/1895 | Cills | 128/203.15 |
| 2,533,065 | 12/1950 | Taplin et al. | 167/65 |
| 2,534,636 | 12/1950 | Stirn | 128/203.15 |
| 2,603,215 | 7/1952 | Arnow | 128/203.15 |
| 2,603,216 | 7/1952 | Taplin et al. | 128/203.15 |
| 2,642,063 | 6/1953 | Brown | 128/203.15 |
| 3,669,113 | 6/1972 | Altounyan et al. | 128/203.15 |
| 3,837,341 | 9/1974 | Bell | 128/203.15 |
| 3,948,264 | 4/1976 | Wilke et al. | 128/203.15 |
| 3,948,264 | 4/1976 | Wilke et al. | 128/203.21 |
| 3,980,074 | 9/1976 | Watt et al. | 128/203.15 |
| 4,265,236 | 5/1981 | Pacella | 128/203.15 |
| 4,265,236 | 5/1981 | Pacella | 128/203.23 |
| 4,353,365 | 10/1982 | Hallworth et al. | 128/203.15 |
| 4,423,724 | 1/1984 | Young | 128/203.15 |
| 4,790,305 | 12/1988 | Zoltan et al. | 128/203.28 |
| 4,811,731 | 3/1989 | Newell et al. | 128/203.15 |
| 4,841,964 | 6/1989 | Hurka et al. | 128/203.15 |
| 4,846,168 | 7/1989 | Abiko et al. | 128/203.15 |
| 4,926,852 | 5/1990 | Zoltan et al. | 128/203.24 |
| 4,935,244 | 6/1990 | Clark | 264/4.1 |
| 4,955,945 | 9/1990 | Weick | 128/203.12 |

FOREIGN PATENT DOCUMENTS

| | | | |
|---|---|---|---|
| 509878 | 2/1955 | Canada | 128/203.15 |
| 2118842 | 11/1972 | Fed. Rep. of Germany | |
| WO82/01470 | 5/1982 | PCT Int'l Appl. | |
| 662277 | 9/1987 | Switzerland | |
| 2165159 | 4/1986 | United Kingdom | |
| 2179260 | 3/1987 | United Kingdom | 128/203.15 |

OTHER PUBLICATIONS

"The Fluid Mechanics of Cromolyn Sodium Inhalers Used for Asthma Prevention", Niemi, Jr., 22-23 Mar. 1979, Conference Notes.

*Primary Examiner*—Edgar S. Burr
*Assistant Examiner*—Kimberly L. Asher
*Attorney, Agent, or Firm*—Marshall, O'Toole, Gerstein, Murray & Borun

[57] ABSTRACT

A disposable device for the administration of powdered inhalation medicament is provided which comprises a rigid medicament reservoir (4) holding a unit dose of medicament (10) and having air inlet means (5,7) and medicament outlet means (8); and closure means (3) which are removable in use; wherein the medicament (10) held in the reservoir (4) is in loose powder form.

5 Claims, 2 Drawing Sheets

DISPOSABLE POWDER MEDICAMENT INHALATION DEVICE WITH PEEL-OFF COVER

This application is a continuation of application Ser. No. 07/541,916, filed Jun. 21, 1990, now abandoned.

This invention relates to a device for the administration of powdered inhalation medicaments, more particularly to such a device which is used for a small number of administrations (for example one) and is then disposed of.

Reusable devices for the administration of powdered inhalation medicaments are well known. For example, UK Patent 1122284 discloses a device for the administration of medicament held in a gelatin capsule, which comprises a capsule-puncturing mechanism and a propeller-shaped capsule holder which rotates during inhalation by a patient to empty medicament from the punctured capsule. Although the device has proved most beneficial to some patients, it is too complicated for others to operate effectively. In addition, the device is expensive to manufacture, and requires regular cleaning of its components which entails disassembly and reassembly of the device.

In order to overcome the disadvantages of reusable devices, a number of disposable inhalation devices have been proposed. UK Patent Application No 2179260 discloses such a device comprising a body defining an endless path communicating with an air inlet and an air outlet. A ball is provided within the endless path which travels around the path upon inhalation by a patient, thus releasing medicament coated on the ball or on the inner surface of the endless path into the inhaled airstream. The device has the disadvantages that the endless path is difficult to manufacture which consequently makes the device expensive, and that some medicaments are not delivered satisfactorily from it, notably those which have a unit dose of comparatively large mass. In addition, there is a danger that the dose delivered to a patient from such a device may vary widely since it will depend upon attrition of the coating by impaction of the ball on the surface. The dose delivered may therefore depend, amongst other things, upon the force with which air is inhaled through the device.

U.S. Pat. No 4,265,236 discloses a disposable nasal inhalation device comprising a length of flexible tubing in which medicament is held, which is formed into a closed loop prior to use. In use, the ends of the tube are separated and a patient inhales through the tube, thus entraining the medicament into the inhaled air. In order to produce the air turbulence necessary to break up aggregations of powder, a preferred form of the device is provided with a small length of pipe within the tube, the pipe having spiral ridges on its inner surface. Not only does this feature increase the cost of the device, but there is also a danger that the pipe may become dislodged and be inhaled by a patient with potentially disastrous consequences. In addition, because of the open nature of the device, there is a risk that powder may fall out of the device between separation of the two ends of the tube and inhalation.

We have now devised a disposable inhalation device which overcomes or substantially mitigates the disadvantages of prior art devices.

According to the present invention, there is provided a disposable device for the administration of powdered inhalation medicament comprising a rigid medicament reservoir holding a unit dose of medicament and having air inlet means and medicament outlet means; and closure means for the inlet and outlet means which are removable in use; characterized in that the medicament held in the reservoir is in loose powder form.

Devices according to the invention have the advantages that they are sufficiently cheap to be disposable, do not have components which could be dislodged and inhaled during use, sufficiently enclose the medicament to prevent it falling out of the device immediately before use, are very simple to use, and are capable of delivering an accurate dose of medicament to a patient.

The air inlet means may comprise one or more openings having a total inlet cross sectional area, and the medicament outlet means may similarly comprise one or more openings having a total outlet cross sectional area. The ratio of the total outlet cross sectional area to the total inlet cross sectional area is preferably in the range of from 1:1 to 1:10, more preferably from 1:2 to 1:4, for example 1:3. We have found that cross sectional areas in the preferred ratio aid break-up of powder aggregates.

We prefer the medicament outlet means to be provided on a raised portion of the device which is adapted to fit between a user's lips for example it may be hemispherical or distorted hemispherical having an oval lateral cross section, so that the raised portion may act as a mouthpiece.

When the reservoir is situated in a raised portion of the device, we particularly prefer the medicament outlet means to be provided on the same raised portion.

We prefer the medicament outlet means to comprise a group of openings in a wall of the reservoir, for example the openings may be arranged in a grid. Grids are preferred because they break up any aggregates of powder as they pass through, and they also retain powder in the device immediately before administration more effectively than a single opening of comparable cross sectional area.

We prefer the air inlet means to comprise an air passageway which connects one or more openings in a surface of the device with the medicament reservoir. The air passageway may join the reservoir tangentially. Two such passageways could be provided on opposite sides of the reservoir so that a swirling motion is imparted to the air in the reservoir during inhalation through the device by a patient.

It is possible to produce the device with very small dimensions. This has the advantages that the medicament may be administered discreetly without embarrassment, very little material is required to produce it thus reducing costs and waste, and a day's dose may be carried conveniently in a small volume. However, when the device is to be used by patients who might swallow it, the body may be of enlarged dimensions, and such a body could be provided with a sufficient number of reservoirs to provide one day's supply of medicament to a patient, for example four. Of course, such a device might be preferred by any patient for yet greater compactness.

Devices according to the invention are useful for the administration of inhalation medicaments where there is a comparatively large mass of active ingredient in each dose, for example sodium cromoglycate and nedocromil sodium, where unit doses are often several milligrams in mass and other disposable devices are not suitable to administer them. However, devices according to the present invention may also be used to administer inhalation medicaments where a comparatively small mass of active ingredient is delivered in each dose, for example steroidal drugs where each unit dose is several hundred micrograms in mass.

The inner surface of the reservoir may be shaped so as to produce air turbulence in use, thus aiding break-up of powder aggregates and dispersion of the powder. For example, a baffle may be provided in the reservoir adjacent to the point at which the air inlet means join it.

Devices according to the invention may be manufactured from plastics material using conventional forming methods, for example vacuum forming or injection moulding.

We prefer the closure means to be a cover sheet which is removably attached to an outer surface of the device. Such a cover sheet preferably seals both the openings of the air inlet mean and the openings of the medicament outlet means. Advantageously, the openings of the air inlet means and the medicament outlet means are situated on one face of the device, in which case the cover sheet need only be of comparably small size.

The closure means may be made of plastics material, metal foil, or a laminate of plastics and metal foil. It may be held on the container by any convenient means, for example glue or heat sealing, and is preferably removable by hand in one piece.

As well as retaining the medicament, the closure means may seal the container from contamination by microorganisms. Thus a sterile device is assured for each administration.

A preferred embodiment of the present invention will now be described, by way of example, with reference to the accompanying drawings, in which.

Figure 1:
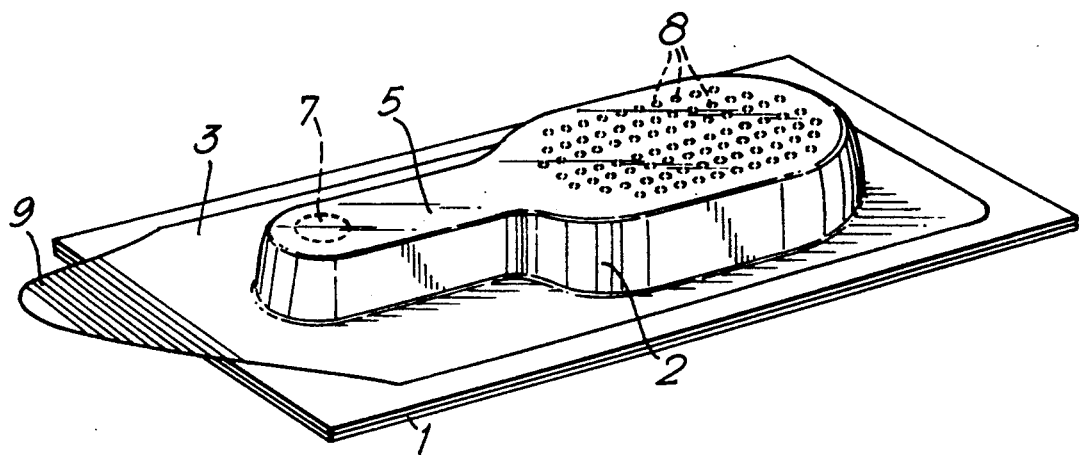
FIG. 1 is a perspective view of a disposable inhalation device according to the invention.
Figure 2:
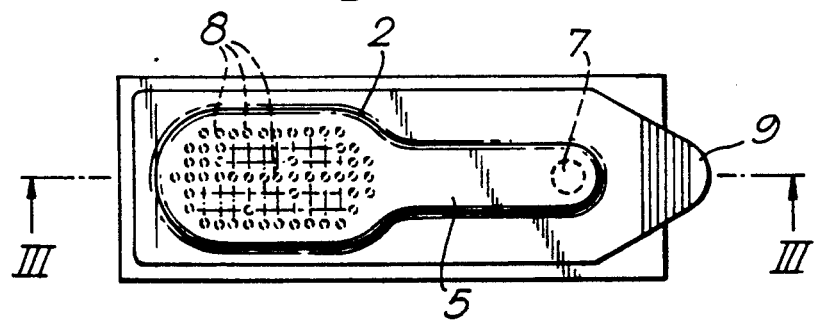
FIG. 2 is a plan view of the device of FIG. 1.
Figure 3:
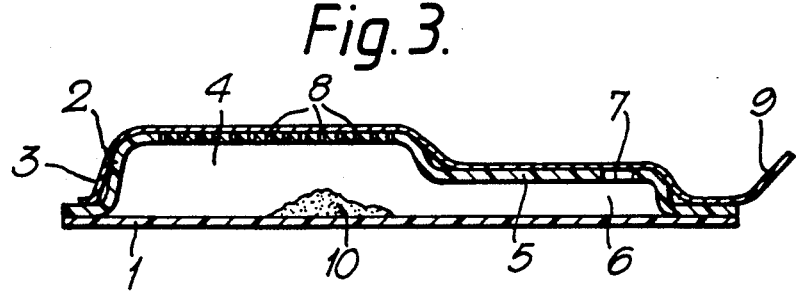
FIG. 3 is a cross sectional view along the line III—III of FIG. 2.

A disposable inhalation device according to the invention comprises a flat plastics rectangular base 1 heat-sealed to a formed plastics upper portion 2, and a removable plastics-metal laminate cover sheet 3 glued to the outer surface of upper portion 2.

Upper portion 2 defines a medicament reservoir 4 having an arm 5 extending from one end. Arm 5 defines an air passageway 6 connecting an air inlet 7 at one end of the arm with medicament reservoir 4 at the other end.

A number of holes 8 arranged in a grid and opening into medicament reservoir 4 are provided on the surface of upper portion 2. This upper surface is shaped so as to fit comfortably between a patient's lips so that it may act as a mouthpiece.

When cover sheet 3 is attached to the device, air inlet 7 and holes 8 are sealed prior to use.

To use the device, a patient simply pulls on a tab portion 9 of cover sheet 3, which consequently peels away from the surface of upper portion 2 to open air inlet 7 and holes 8. The mouthpiece is then offered up to the patient's lips, whereupon inhalation through holes 8 results in air being drawn into air inlet 7, along passageway 6 and into medicament reservoir 4 where unit dose of medicament 10 is entrained by the airstream. The entrained medicament then passes out of the device through holes 8 and is administered to the patient.

Figure 4:
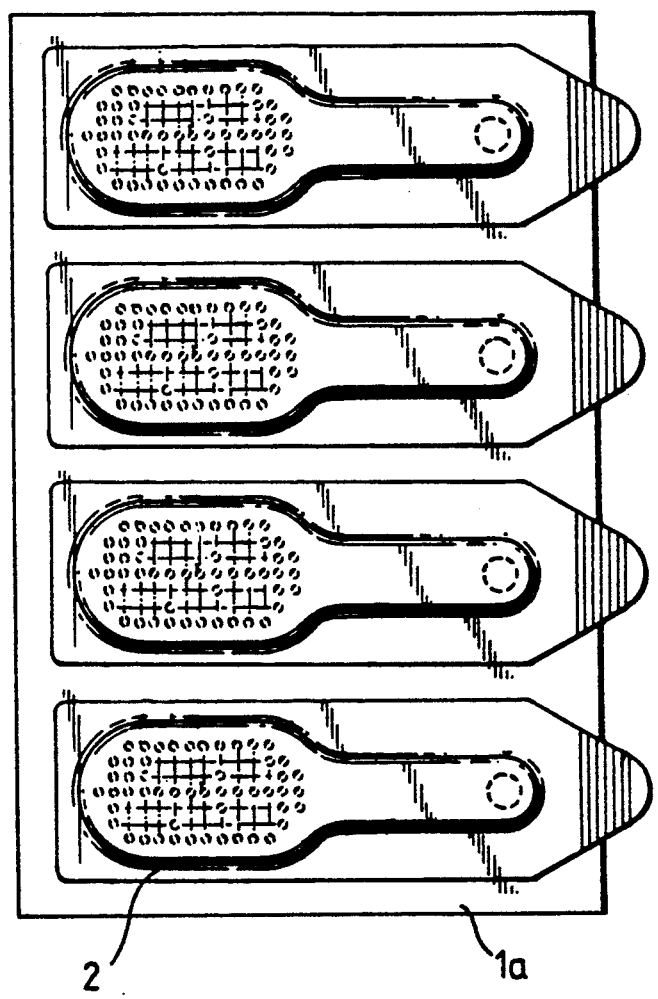
FIG. 4 is a perspective view of a disposable inhalation device according to the invention having a plurality of reservoirs.

FIG. 4 illustrates a further embodiment of the device according to the invention wherein base (1a) is of enlarged dimensions and is provided with four upper portions (2) each defining a medicament reservoir.

What is claimed is:

1. A disposable device for the administration of powdered inhalation medicament to a patient, said device comprising:
    (a) a flat base member;
    (b) a raised upper portion attached to the base member defining a rigid medicament reservoir holding a unit dose of medicament in loose powder form, said reservoir acting as a mouthpiece;
    (c) an arm extending from the medicament reservoir defining an air passageway connecting an air inlet provided at one end of the arm with the medicament reservoir at the other end;
    (d) medicament outlet means comprising a group of openings provided in a wall of the medicament reservoir through which the medicament is inhaled; and
    (e) closure means comprising a cover sheet peelably attached to an outer surface of the device which seals both the openings of the air inlet means and the medicament outlet means;
    such that in use upon removal of the closure means and inhalation through the mouthpiece by a patient, air is drawn into the air inlet and along the air passageway into the reservoir causing medicament to be entrained in the air stream and inhaled by the patient.

2. A disposable device according to claim 1, wherein the air inlet means comprise one or more openings having a total inlet cross sectional area and the medicament outlet means comprise one or more openings having a total outlet cross sectional area; further characterized in that the ratio of the total outlet cross sectional area to the total inlet cross sectional area is in the range of from 1:1 to 1:10.

3. A disposable device according to claim 1, further characterized in that the device is provided with a sufficient number of reservoirs to provide one day's supply of medicament to a patient.

4. A disposable device according to claim 1, further characterized in that the medicament held by the reservoir is selected from the group consisting of sodium cromoglycate and nedocromil sodium.

5. A disposable device according to claim 1, further characterized in that an inner surface of the reservoir is provided with a baffle so as to produce air turbulence in use.

* * * * *